United States Patent [19]

Sinn

[11] Patent Number: 5,390,782
[45] Date of Patent: Feb. 21, 1995

[54] NEEDLE SHIELD DEVICE FOR SURGICAL PACKAGES

[75] Inventor: Hans-Jurgen F. Sinn, Fairfield, Conn.

[73] Assignee: United States Surgical Corporation, Norwalk, Conn.

[21] Appl. No.: 240,948

[22] Filed: May 10, 1994

Related U.S. Application Data

[63] Continuation of Ser. No. 901,271, Jun. 19, 1992, abandoned.

[51] Int. Cl.$^6$ ............................................. A61L 17/02
[52] U.S. Cl. ................................. 206/63.3; 206/380
[58] Field of Search ................... 206/63.3, 63.5, 1.5, 206/380, 382, 383, 339, 491, 492

[56] References Cited

U.S. PATENT DOCUMENTS

| | | |
|---|---|---|
| 2,993,589 | 7/1961 | Zoller et al. . |
| 3,136,418 | 6/1964 | Stacy et al. . |
| 3,162,307 | 12/1964 | Regan . |
| 3,444,994 | 5/1969 | Kaepernik et al. . |
| 3,857,484 | 12/1974 | Thyen . |
| 3,876,068 | 4/1975 | Sonnino ............................ 206/63.3 |
| 3,939,969 | 2/1976 | Miller . |
| 4,063,638 | 12/1977 | Marwood . |
| 4,120,395 | 10/1978 | Mandel et al. . |
| 4,249,656 | 2/1981 | Cerwin et al. . |
| 4,253,563 | 3/1981 | Komarnycky . |
| 4,284,194 | 8/1981 | Flatau . |
| 4,391,365 | 7/1983 | Batchelor . |
| 4,406,363 | 9/1983 | Aday . |
| 4,412,613 | 11/1983 | Kubas ............................... 206/63.3 |
| 4,412,614 | 11/1983 | Ivanov et al. . |
| 4,413,727 | 11/1983 | Cerwin . |
| 4,427,109 | 1/1984 | Roshdy . |
| 4,483,437 | 11/1984 | Cerwin et al. . |
| 4,491,218 | 1/1985 | Aday . |
| 4,496,045 | 1/1985 | Ferguson et al. . |
| 4,533,041 | 8/1985 | Aday et al. . |
| 4,555,016 | 11/1985 | Aday et al. . |
| 4,572,363 | 2/1986 | Alpern . |
| 4,574,948 | 1/1986 | Huck et al. . |
| 4,700,833 | 10/1987 | Smith ......................... 206/63.3 X |
| 4,708,241 | 11/1987 | Black, deceased ............ 206/63.3 |
| 4,884,681 | 12/1989 | Roshdy et al. . |
| 4,896,767 | 1/1990 | Pinheiro . |

FOREIGN PATENT DOCUMENTS 0458432 11/1991 European Pat. Off. .

*Primary Examiner*—Jacob K. Ackun, Jr.

[57] ABSTRACT

A needle shield for use in conjunction with a suture package includes foldable panels of puncture-resistant material bendable at perforated fold lines to wrap around a needled suture retainer. A tabbed locking means secures the needle shield in a closed configuration. The needle retainer and shield are loaded into an outer envelope and sterilized to provide a sterile packaged suture. A method of assembling the package is disclosed wherein a needled suture is loaded into the retainer, the needle shield is folded around the retainer, and the needle retainer and needle shield are loaded into and sealed within an outer envelope.

18 Claims, 4 Drawing Sheets

NEEDLE SHIELD DEVICE FOR SURGICAL PACKAGES

This is a continuation of application Ser. No. 97/901,271, filed on Jun. 19, 1992, now abandoned.

BACKGROUND OF THE INVENTION

1. Field of the Invention

The present invention relates to surgical suture-needle packages, and more particularly to a needle shield device for protecting the tip of the needles from damage and to eliminate the possibility of accidental puncturing of the outer envelope enclosing the needled sutures retained therein.

2. Discussion of the Prior Art

Packaging devices for needles and suture needle assemblies generally include a retainer to enclose or hold the needles and/or sutures, and an outer envelope in which the retainer is sealed. The outer envelope maintains the sterility of the needles and sutures. In some cases a foil outer pouch is used so as to maintain a constant atmospheric condition inside the envelope to prevent drying of the suture. The retainer generally includes a fold-over flap or a cover which at least partially encloses the needles or the needle tips in the package. In many cases, the flap is integrally formed as part of the retainer so that the flap or cover comprises a tear away portion which exposes the needles upon opening of the retainer.

Several tear away type needle covers for use with surgical suture-needle assembly retainers are provided in the prior art. These retainers generally comprise a panel having either perforations or score lines which facilitate tearing a portion of the panel from the retainer to expose the needles after the retainer is opened. After the tear away cover or flap is removed, the needle and suture assembly may be removed from the retainer in the conventional manner.

In the prior art, several retainers having tear away cover flaps are disclosed, such as U.S. Pat. No. 4,063,638 to Marwood. The retainer in Marwood comprises a three panel retainer, where the suture is wound and held at the center panel and the needle is held in an outer panel. A panel having the tear away flap is provided on the outer panel opposite the needle retaining panel, and the tear away flap is folded over the sutures followed by the needle retaining flap. Upon opening the retainer, the flap is torn away, thus revealing the needle so that the needle may be removed in the conventional manner.

U.S. Pat. No. 4,406,363 to Aday, U.S. Pat. No. 4,412,614 to Ivanov et at., and U.S. Pat. No. 4,427,109 to Roshdy disclose retainers with tear away flaps or covers similar to that disclosed in Marwood above.

Another type of retainer prevalent in the prior art provides a fold over flap which covers the needles within the package. When the package is opened, the fold over flap is unfolded to reveal the needles so that the needles may be removed in the conventional manner. Such a device is disclosed in U.S. Pat. No. 4,574,948 to Huck et at., which provides a retainer in which the suture-needle assembly is secured on one panel and the needles are secured on a second panel. A fold-over flap is provided to cover the needles to prevent pricking of the user and to prevent damage to the needle tips. As the retainer is opened, the fold over flap is unfolded or torn to reveal the needles so that the needles may be removed in a conventional manner. A similar type device is disclosed in U.S. Pat. No. 4,708,241 to Black.

Other fold over cover flaps for retaining devices are disclosed in U.S. Pat. No. 4,120,395 to Mandel et al., U.S. Pat. No. 4,391,365 to Batchelor, and U.S. Pat. No. 4,884,681 to Roshdy et al. Mandel et al. and Roshdy et al. disclose a cover flap to which the needles are attached, so that as the flap is folded over the needles are covered and protected. Batchelor discloses a device similar to Huck et al. above.

Another type of suture retainer employs a configuration which comprises a coiled passageway for containing a length of suture thread. The thread is attached to a needle positioned along side the outer surface of the retainer. A retainer of this type is described in U.S. application Ser. No. 07/566,263 filed Aug. 13, 1990.

The devices disclosed in the prior art suffer from several disadvantages in which the risk of accidental pricking of the user's finger by the needle point is not significantly reduced or eliminated, especially where the needles are positioned on the outside of the retainer and have exposed tips. Further, many of these devices suffer a disadvantage in that the cost of packaging is increased due to the necessity for additional packaging material as well as increasing the number of packaging steps during assembly.

Another problem associated with the exposed needle tip is that it may puncture the outer envelope, thereby allowing entry of contaminants or release of volatile treating agents. A conditioning agent is usually incorporated into packages for certain types of sutures (e.g. collagen sutures) to keep them supple and to maintain good handling characteristics. Because the conditioning agent includes volatile liquid, the retainer and needled sutures need to be enclosed in the impermeable foil envelope, which is sealed air tight around its periphery. In use, the surgeon tears open the foil envelope, removes the retainer, then removes a needle, thereby pulling the suture out of the retainer.

When the suture packages are stacked and handled during shipment, it is possible for the sharp point of the needle to penetrate the outer foil package. Such a puncture will compromise sterility and, in the case of collagen sutures, will permit the volatile conditioning fluid to escape by means of evaporation, thus resulting in drying of the sutures and thereby rendering them unusable.

SUMMARY OF THE INVENTION

A needle shield is provided herein for use in packages for needled sutures. The needle shield comprises a sheet of substantially puncture resistant material which includes a plurality of foldably connected panels, the sheet being configured and dimensioned so as to at least partially surround the needled suture retainer and to cover at least the pointed tips of the needles when the panels are folded. In addition, a package is provided consisting of a needled suture retainer surrounded by a needle shield and all enclosed within an outer envelope. A method of assembling the needle shield and package is also disclosed.

A further feature of the present invention is a locking means associated with at least one of the needle shield panels. The locking means includes at least one tab and a slot for receiving the tab. Alternatively, the locking means can include a first tab defined by a slit in one of the panels, and a first-tab reception means on another of the panels, the first-tab reception means including a second tab having a projection for insertion through the slit and at least one flap, the first tab being insertable underneath the flap.

The shield advantageously prevents the plurality of needle points from piercing the outer envelope of the package by enclosing the retainer, particularly about the needles.

DETAILED DESCRIPTION OF PREFERRED EMBODIMENT(S)

Figure 1:
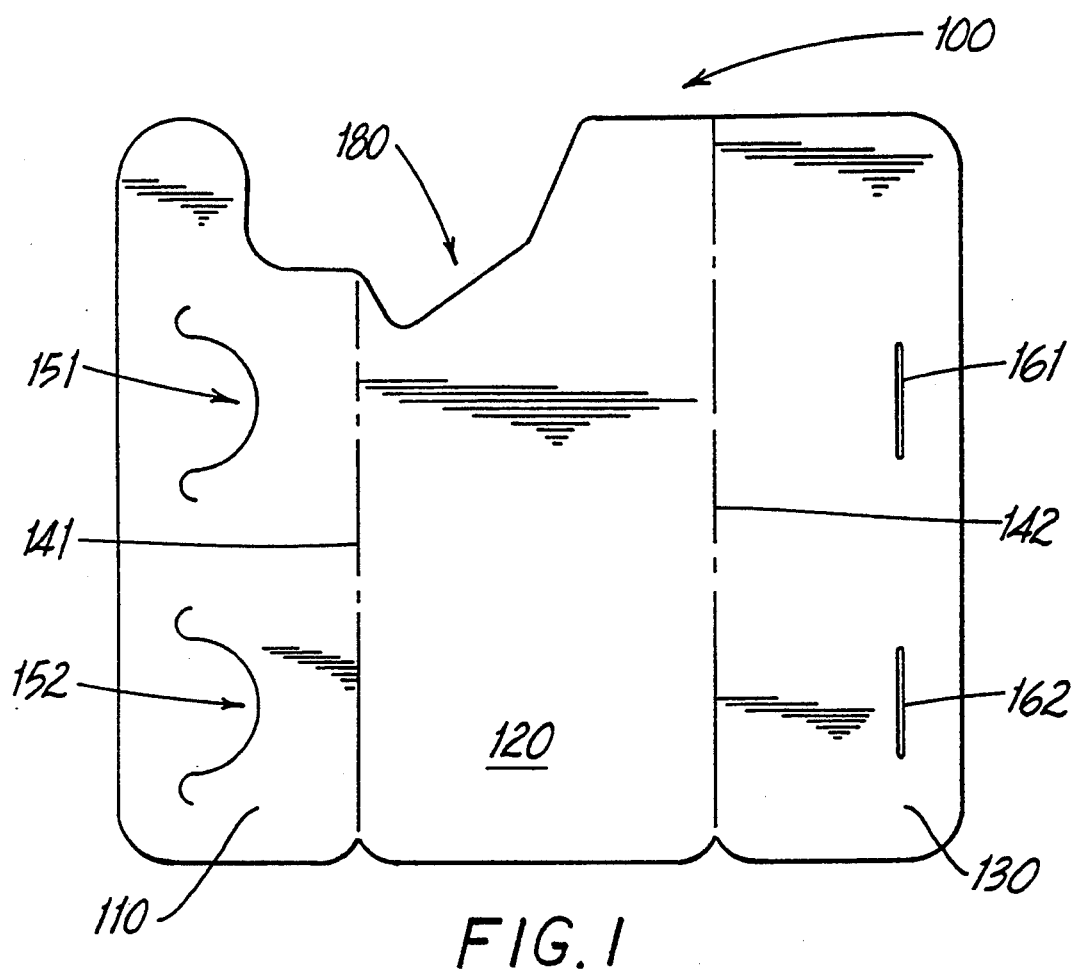
FIG. 1 is a plan view of one embodiment of the needle shield.

Referring now in specific detail to the drawings, in which like reference numerals identify similar or identical elements throughout the several views, FIG. 1 shows the needle shield 100 of the present invention, which comprises a flat sheet of substantially puncture-resistant material, which is a part of the entire package separate from and in addition to the retainer and the outer envelope. The puncture-resistant material is preferably a material such as TYVEK (a registered trademark of DuPont), which comprises spun bonded polyolefin fibers pressed together to form a fibrous sheet. Other suitable materials, such as plastic sheet (e.g., polycarbonate, polystyrene, polyethylene or polypropylene films), cardboard, or stiff paper stock may be employed if sufficiently resistant to puncture.

Needle shield 100 comprises a center panel 120 to which end panels 110 and 130 are attached along perforated fold lines 141 and 142, respectively. Panel 110 includes tabs 151 and 152 formed by arcuate slits in the panel. Panel 130 includes openings or slots 161 and 162 to receive, respectively, tabs 151 and 152 when the needle shield is folded and closed. A cut-away portion 180 is provided to allow the user to see the position of the butt-ends of the needles while the needle points are positioned under the shield.

Figure 2:
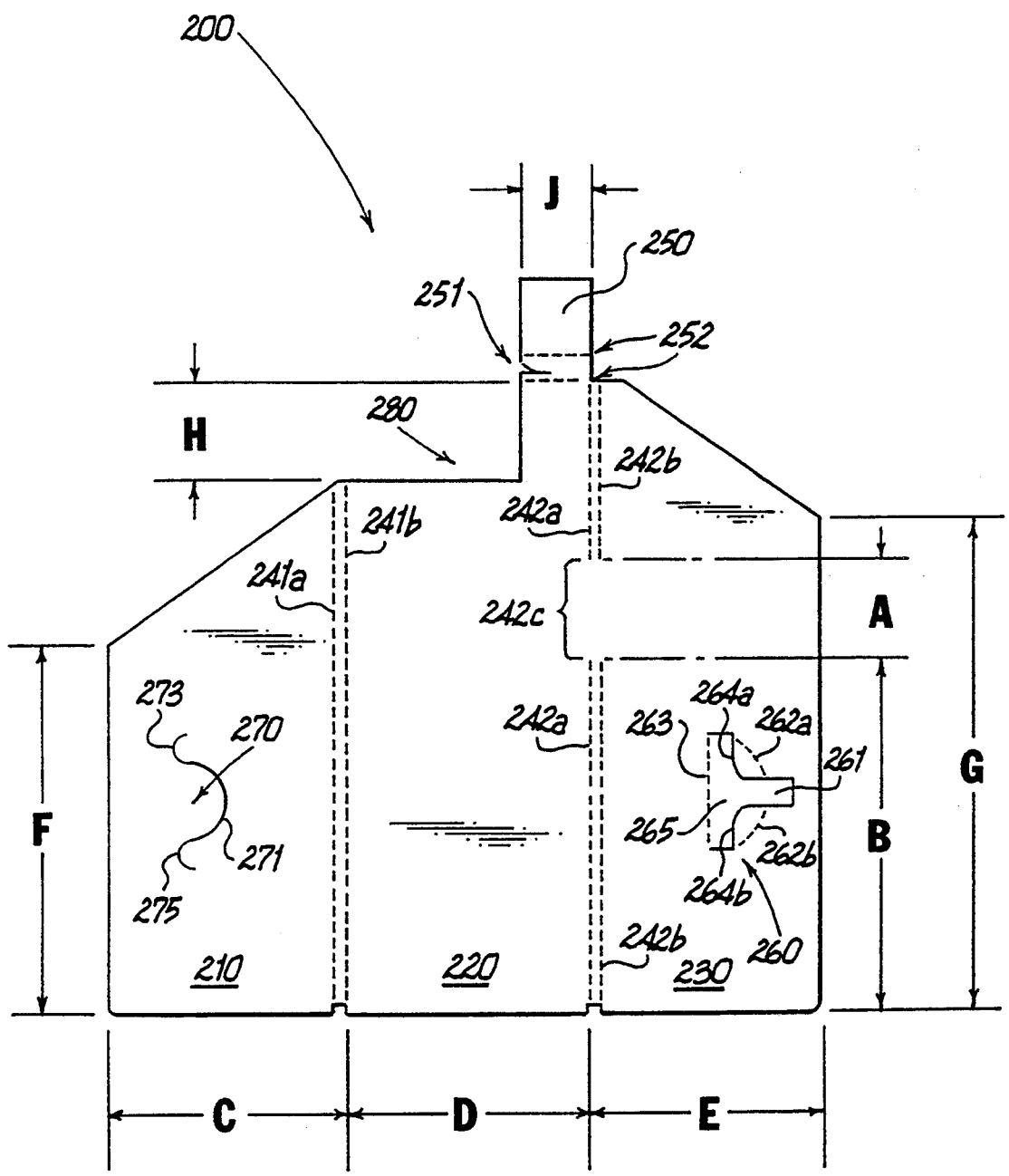
FIG. 2 is a plan view of another embodiment of the needle shield.

FIG. 2 illustrates another embodiment of the needle shield 200. Needle shield 200 includes center panel 220 to which end panels 210 and 230 are attached along scored double fold lines. Fold lines 241a and 241b attach panel 210 to panel 220. Fold lines 242a and 242b attach panel 230 to panel 220. A portion 242c of fold lines 242a and 242b should be non-scored to prevent protrusion therethrough by the tips of the needles. The non-scored portion 242c may have a length A of from about 1.19 inches to about 1.44 inches, and may be spaced apart from the bottom edge by a distance B of from about 1.24 inches to about 1.49 inches. The fold lines may also be fabricated as a single scored lines, as shown in FIG. 1 for the needle shield 100. However, double scored lines provide a space or gusset between the individual lines to accommodate the thickness of the suture retainer when enveloped by the needle shield, thus permitting the panels to lay flat when folded.

Projection 250 is a fold-over flap to help maintain the suture retainer positioned within the folded needle shield 200 and to cover and protect the butt end of the first needle. Projection 250 includes a notch 251 and scored fold lines 252.

Also included is a cut-away portion 280 to allow the user to see the position of the butt-ends of the needles with the needle points covered by panel 280.

The needle shield 200 may be of any dimensions suitable for its purpose. Some suitable dimensions are presented below in Table 1.

TABLE I

| Feature | FIG. Indicator | Dimensions, (inches) From about | To about |
|---|---|---|---|
| With of panel 210 | C | 1.06 | 1.53 |
| Width of Panel 220 | D | 1.47 | 1.53 |
| Width of panel 230 | E | 1.45 | 1.50 |
| Height of outer edge of panel 210 | F | 2.10 | 2.60 |
| Height of outer edge of panel 230 | G | 2.68 | 3.23 |
| Height of cut-away portion 280 | H | 0.77 | 0.78 |
| Width of projection 250 | J | 0.41 | 0.42 |

Figure 3:
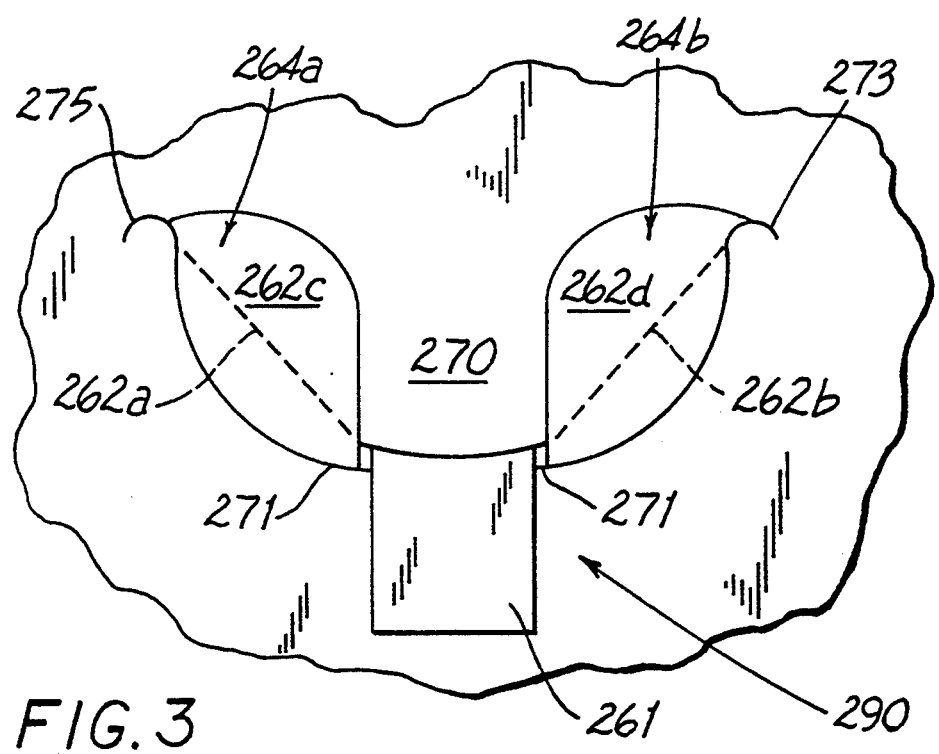
FIG. 3 is a plan view of the locking means in a closed configuration.
Figure 6:
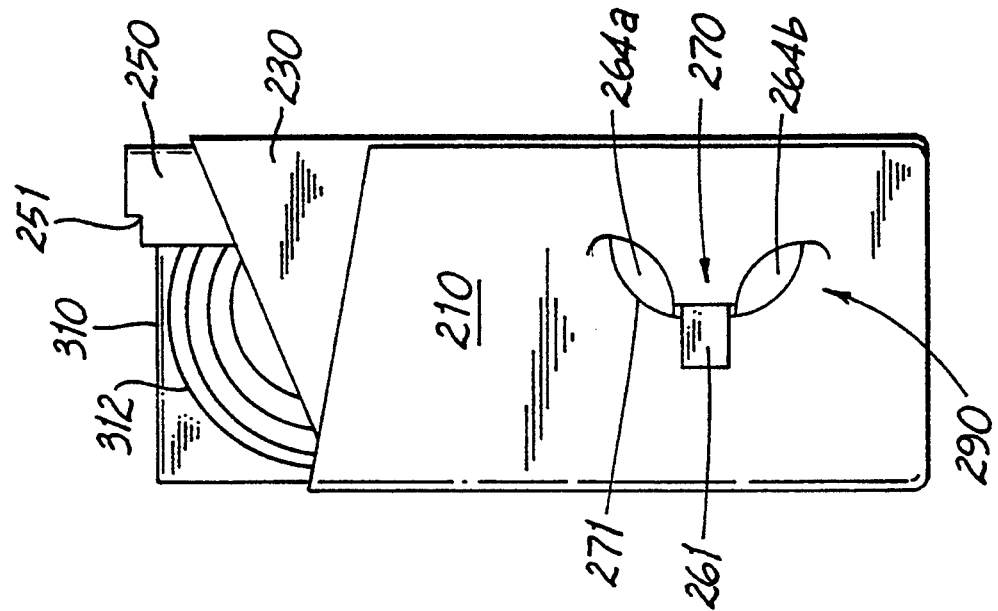
FIGS. 5 and 6 show front and back views of the needle shield in conjunction with needled sutures held by a retainer.

A unique feature disclosed herein is the tabbed locking means 290 illustrated in a locked position in FIGS. 3 and 6. Features of the locking means in unlocked position are shown in FIG. 2, to which is now referred. Panel 210 includes a tab 270 created by arcuate slit 271 preferably having minor reverse arcuate sections 273, 275. Panel 230 includes a cooperating engagement means 260, also defined by a slit in the panel. The engagement means 260 includes a tab 265 having a relatively narrow laterally projecting ramp strip 261. Referring also now to FIG. 3, tab 265 is foldable along perforated fold line 263. Arcuate edges 264a and 264b and bendable fold lines 262a and 262b, respectively define arcuate flaps 262c and 262d. FIG. 3 illustrates the locking means when fully engaged, a description of the locking procedure being given below.

Figure 4:
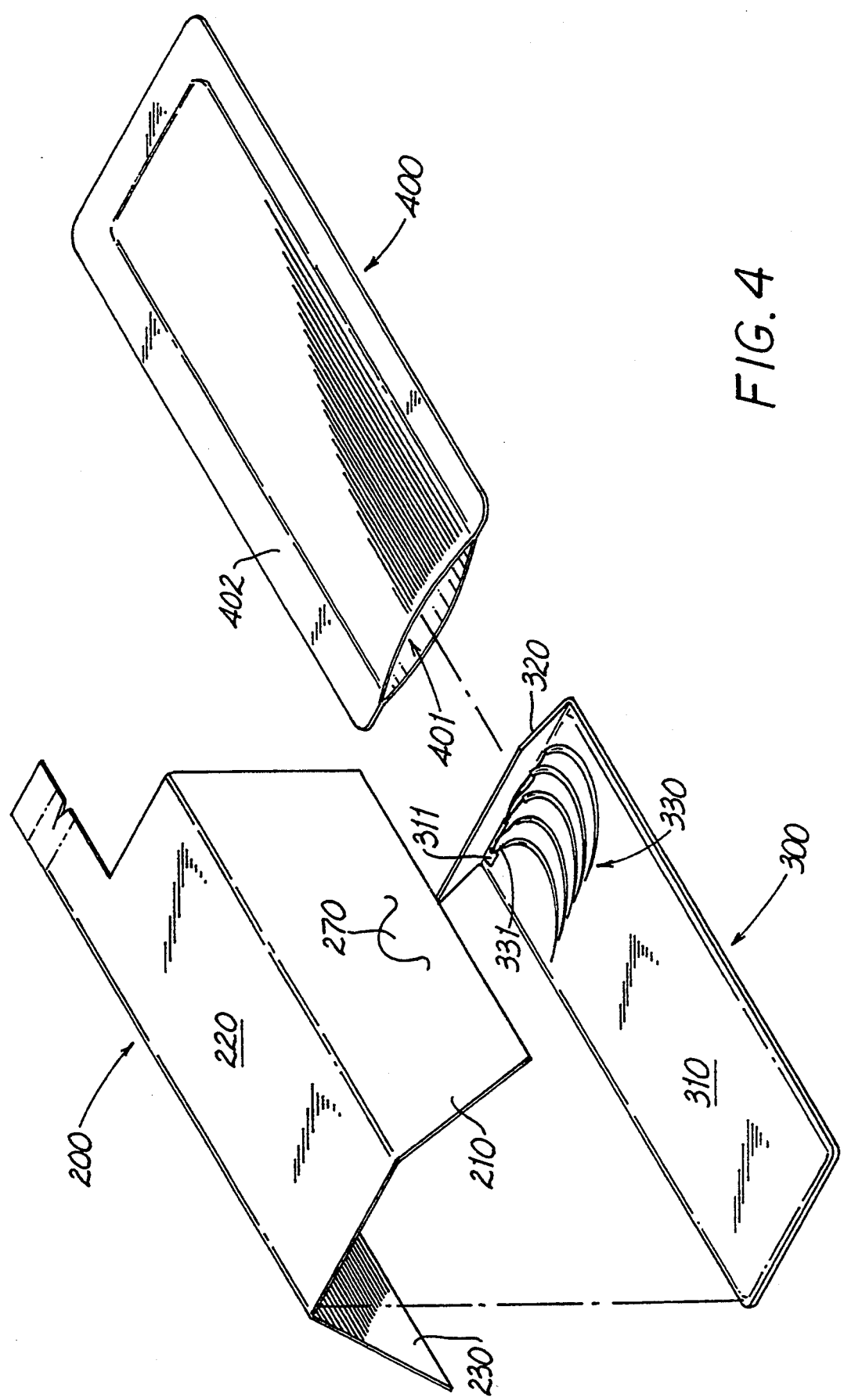
FIG. 4 is an exploded perspective view of a suture package assembly including a needle shield of the present invention.

FIG. 4 illustrates a package assembly for holding needled sutures. Needled sutures include surgical needles 330 attached to sutures 331. The sutures can be fabricated from bioabsorbable or non-bioabsorbable material. Suitable non-bioabsorbable materials include silk, cotton, and synthetic materials such as Dacron (DuPont), nylon, polypropylene or other polyolefins and polyesters. By way of example only, suitable bioabsorbable materials include catgut or other collagenous material, and synthetic materials such as homopolymers and copolymers of glycolide, lactide, dioxanone, caprolactone and trimethylene carbonate, or mixtures and blends thereof. The needle shield is especially advantageous for use in conjunction with collagenous sutures, which require a conditioning agent to maintain suppleness and are susceptible to drying out if the outer foil envelope is punctured. The sutures with conditioning fluid are held inside retainer 300. The retainer 300 includes a body portion 310 having an interior space in which the sutures are stored, and a fold-over flap 320 for coveting and holding the butt ends of needles 330 in position along the outside surface of the body portion 310. One end of each suture extends through opening 311 in the body portion 310 and is attached to the butt end of the respective needle 330. The interior of the body can have a molded spiral channel 312 (see FIG. 6) for holding the suture. The needle shield 200 is illustrated in the partially opened configuration. The retainer 300 with the needled sutures is placed in the needle shield 200, which is then closed and locked. The closed and locked shield is illustrated in FIGS. 5 and 6, to which we now refer.

Figure 5:
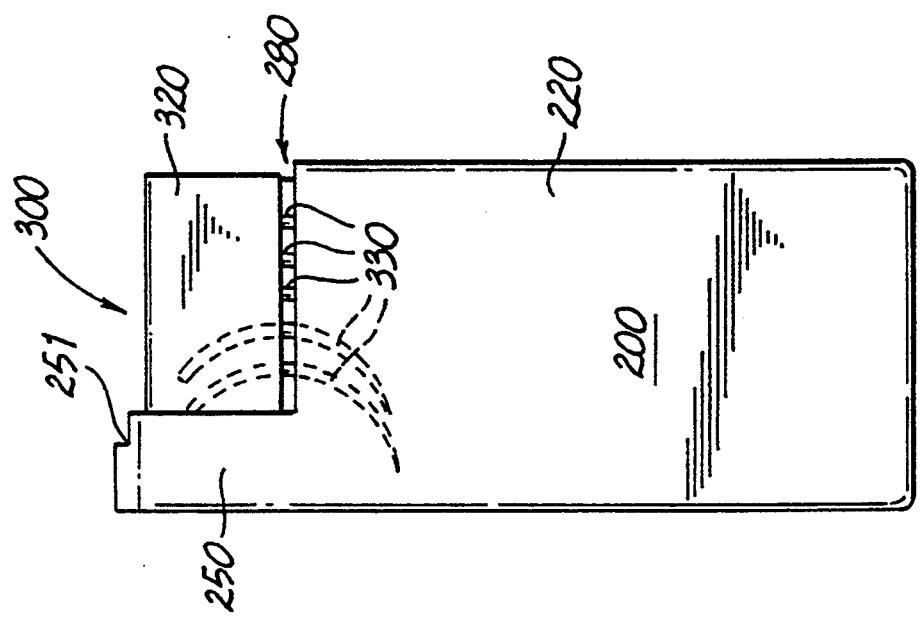

FIG. 5 shows one side of the shielded suture retainer. Flap 320 covers a portion of the needles. The height H of the cut-away portion 280 of the shield preferably exceeds the height of flap 320 so as to leave a gap through which the needles 330 can be seen by the user. Projection 250 is folded over the suture retainer 300 and underneath panel 230 on the opposite side, as shown in FIG. 6. Projection 250 may be easily opened by the user by lifting up flap 320 so as to expose the needles 330. The closed locking means is shown in FIG. 3, to which we additionally refer. When the needle shield 200 is closed panel 230 is first folded over. As panel 210 is folded over panel 230 ramp 261 is inserted through slit 271, which ramp 261 then overlaps. Flaps 264a and 264b may be bent upward at fold lines 262a and 262b, respectively, to permit tab 270 to be inserted underneath flaps 264a and 264b. The resulting locked configuration as shown in FIG. 3 presents a more secure engagement than the simple tab in slot arrangement as shown in FIG. 1, yet is easily locked and unlocked. The ramp feature 261 is especially advantageous when the suture retainer has a rough or non-flat surface, as for example with retainers having a molded spiral channel, since the ramp 261 prevents engagement of tab 270 from being blocked by the ribbed surface of the molded spiral channel 312. Alternatively, ramp 261 need not overlap slit 271, but may simply lie across the surface of the molded spiral channel 312. Ramp 261 is particularly advantageous for guiding the arcuate tab of slit 271 into engagement. Also, the entire lock is formed by simple slits without any mass being removed or added.

Referring again to FIG. 4, the shielded retainer is then inserted through opening 401 of outer envelope 400 which is partially sealed around periphery 402. Envelope 400 can be fabricated from metal foils (e.g., aluminum foil) or polymeric materials, especially plastic laminates. Sterilization of the packaged needled sutures is usually performed during the packaging process, and opening 401 can then be sealed air tight to prevent contamination. Alternatively, the needled sutures can be sterilized after the packaging process is completed, by means of irradiation with gamma rays in accordance with known sterilization procedures. The shield 200 will prevent the sharp points of the needles 330 from puncturing foil package 400, thus preventing suture drying caused by release of conditioning fluid, and suture contamination caused by entry of microorganisms.

The features shown in the above embodiments need not be limited to the specific embodiments in which they are illustrated. For example, the locking means of the needle shield 200 may be incorporated into the needle shield 100, and vice versa.

While the invention has been particularly shown and described with reference to the preferred embodiments, it will be understood by those skilled in the art that various modifications and changes in form and detail may be made therein without departing from the scope and spirit of the invention. Accordingly, modifications such as those listed above, but not limited thereto, are to be considered within the scope of the invention.

What is claimed is:

1. In combination:
   at least one surgical needle-suture combination:
   a retainer member on which said surgical needle and suture are retained with at least a portion of the needle tip exposed; and,
   a needle shield fabricated from a sheet of puncture resistant material which includes a first panel having at least two end panels foldably connected thereto, said sheet being separably positioned in adjacent contacting relation with said retainer member so as to at least partially surround the retainer member and to cover at least the pointed tip of said at least one surgical needle when said panels are folded at least partially around the retainer member.

2. The needle shield of claim 1, wherein said combination further includes a locking means associated with at least one of said panels for releasably joining one of said panels to another of said panels.

3. The combination of claim 2, wherein said locking means includes at least one tab.

4. The combination of claim 3 wherein said tab is defined by a slit in one of said end panels.

5. The combination of claim 4, further including a slot for receiving said tab when said panels are folded.

6. The combination of claim 2, wherein said locking means includes a first tab defined by a slit in one of said end panels, and a reception means in the other of said end panels for receiving said first tab, said first-tab reception means including at least one flap and a second tab having a projection for insertion through said slit, said first tab being insertable underneath said flap.

7. The combination of claim 1, wherein said panels are connected along scored lines.

8. The combination of claim 7, wherein each connection between panels comprises two parallel scored lines spaced apart from each other a distance sufficient to accommodate the thickness of said suture retainer when said needle shield is folded.

9. In combination;
   surgical needle suture retainer;
   at least one surgical needle retained by said needle suture retainer and having a pointed tip exposed on an outside surface of said needle suture retainer; and
   a needle shield, said needle shield being a sheet of puncture resistant material which includes a first panel having first and second end panels foldably connected to said first panel, said sheet being positioned adjacent said needle suture retainer with said first and second end panels folded at least partially therearound to at least partially surround said needle suture retainer so as to cover at least the pointed tip of said at least one surgical needle, said sheet being separable from said needle suture retainer.

10. The combination of claim 9, wherein said needle shield further comprises:
    a first tab defined by a slit in said first end panel, and a first-tab reception means on said second end panel for receiving said first tab, said first-tab reception means including at least one flap and a second tab having a projection for insertion through said slit, said first tab being insertable underneath said flap.

11. The combination of clam 10, wherein said first end panel folds over said second end panel.

12. A needled-suture package, which includes:
    a) at least one needle suture combination;

b) a retainer for said needle suture combination, the needle of the needle suture combination being retained on said retainer; and c) a needle shield which includes a sheet of puncture resistant material which includes a plurality of foldably connected panels, said sheet at least partially surrounding said retainer and being separable therefrom and covering at least the pointed tip of the needle of said at least one needle suture combination when said panels are folded.

13. The needled-suture package of claim 12, further including an outer envelope for containing both said retainer and said needle shield.

14. The needled-suture package of claim 13, wherein said outer envelope is fabricated from a metal foil.

15. The needled suture package of claim 12, wherein said suture is treated with a conditioning agent.

16. The needled suture package of claim 15, wherein said suture is fabricated from a collagenous material.

17. The needle-suture package of claim 12 wherein said material which is resistant to puncture by a needle comprises spun bonded polyolefin fibers pressed together to form a fibrous sheet.

18. The needle-suture package of claim 12 wherein said material which is resistant to puncture by a needle is selected from the group consisting of polycarbonate, polystyrene, polyethylene, and polypropylene.

* * * * *